United States Patent [19]

Metcalf et al.

[11] 4,325,877
[45] Apr. 20, 1982

[54] PRODUCTION OF INTERMEDIATES FOR ENZYME INHIBITORS

[75] Inventors: Brian W. Metcalf, Mason; Jerry L. Adams, West Chester, both of Ohio

[73] Assignee: Richardson-Merrell Inc., Wilton, Conn.

[21] Appl. No.: 160,057

[22] Filed: Jun. 16, 1980

[51] Int. Cl.³ .................... C07C 117/08; C07C 69/74; C07C 69/66
[52] U.S. Cl. .................................. 260/349; 560/105; 560/174
[58] Field of Search ................ 260/349; 560/105, 174

[56] References Cited
PUBLICATIONS

Price et al., J. Org. Chem., vol. 30, pp. 2064 to 2067 (1965).
Rappe, Chem. Abstracts, vol. 54, cols. 17259 to 17260 (1960).
Barton et al., Chem. Abstracts vol. 57, cols. 909–910 (at col. 910 between h and i) 1962.
Chemical Abstracts, Eighth Collective Index, subjects Tripet-Z, p. 32647S.

*Primary Examiner*—John M. Ford
*Assistant Examiner*—Robert C. Whittenbaugh

*Attorney, Agent, or Firm*—John J. Kolano; Raymond A. McDonald; Gary D. Street

[57] ABSTRACT

5-Amino-4-oxo-pentanoic acids of the formula

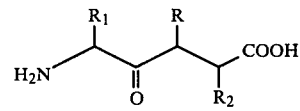

wherein R is $CF_3$, $CHF_2$ or $CH_2F$; $R_1$ is H or akyl of 1–4 carbon atoms; and $R_2$ is H or alkyl or 1–4 carbon atoms or benzyl, which are intermediates to ACE inhibitors or elastase inhibitors, are produced by reacting a 1-(methylthio)-1-methylsulfinyl)-2-$R_1$-ethylmetal with an ester of a 3-R-acrylic acid; optionally $R_2$-alkylating the thus-produced ester enolate anion of 4-(methylsulfinyl)-4-(methylthio)-5-$R_1$R-pentanoic acid followed by splitting off of methylsulfinic acid; reacting the thus-produced 2-$R_2$-5-$R_1$-4-(methylthio)-3-R-4-pentenoic acid ester with a source of $Br^+$ to produce a 5-bromo-substituted acid or ester thereof otherwise corresponding to the desired 5-amino-4-oxo-pentanoic acid; and replacing the bromine atom with an amino group, e.g., via the corresponding 5-azido- and 5-N-acylamino- compounds, with hydrolysis of the ester group, if still remaining.

5 Claims, No Drawings

PRODUCTION OF INTERMEDIATES FOR ENZYME INHIBITORS

BACKGROUND OF THE INVENTION

This invention relates to a novel process for the production of 5-bromo- and 5-amino-4-oxo-pentanoic acid intermediates for the production of angiotensin converting enzyme (ACE) inhibitors and elastase inhibitors and to novel compounds produced therein.

In the prior application of Bey, Metcalf & Wiseman, Ser. No. 043,864, filed May 30, 1979, there is disclosed novel 5-amino-4-oxo acids, which are intermediates for the production of ACE inhibitors, of Formula I

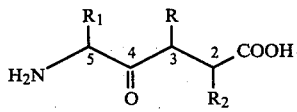

wherein R is $CF_3$, $CHF_2$ or $CH_2F$; $R_1$ is H or alkyl of 1–4 carbon atoms and $R_2$ is H. In the concurrently filed application of Bey and Metcalf entitled "Novel Enzyme Inhibitors" Ser. No. 160,111, June 16, 1980, now U.S. Pat. No. 4,277,395, there are disclosed corresponding compounds of Formula I wherein $R_2$ is alkyl of 1–4 carbon atoms or benzyl, as intermediates for the production of analogous alkyl and benzyl substituted ACE inhibitors and elastase inhibitors. The disclosures of the aforesaid applications are incorporated herein by reference.

It is an object of this invention to provide a novel process for the production of the compounds of Formula I. Another object is the provision of a process for the production of the corresponding 5-bromo compounds and esters thereof which are convertible to the compounds of Formula I. Another object is the provision of novel compounds produced in these processes. Other objects will be apparent to those skilled in the art.

SUMMARY OF THE INVENTION

In a first process aspect, this invention relates to a process for the production of 5-bromo-3-oxo-pentanoic acids of the formula wherein R is $CF_3$, $CHF_2$ or $CH_2F$; $R_1$ is H or alkyl of 1–4 carbon atoms and $R_2$ is H, alkyl of 1–4 carbon atoms or benzyl, which comprises the steps of:

(a) reacting a 1-methylthio-1-methylsulfinyl-2-$R_1$-ethyllithium, -sodium or potassium with an ester of a 3-R-acrylic acid to give an ester enolate anion of 5-$R_1$-4-methylsulfinyl-4-methylthio-3R-pentanoic acid which, when compounds in which $R_2$ is hydrogen are desired, is treated with a proton source and which, when compounds in which $R_2$ is other than hydrogen are desired, is treated with an alkylating or benzylating agent;

(b) heating the thus-produced ester of 2-$R_2$-5-$R_1$-4-methylsulfinyl-4-methylthio-3-R-pentanoic acid, thereby splitting methylsulfinic acid therefrom; and (c) reacting the thus-produced ester of 2-$R_2$-5-$R_1$-4-methylthio-3-R-4-pentanoic acid with a source of $Br^+$ under aqueous conditions, thereby producing the desired 5-bromo-4-oxo-pentanoic acid.

In a second process aspect, this invention relates to a process comprising the further steps of:

(d) reacting the thus-produced ester of 5-bromo-5-$R_1$-2-$R_2$-4-oxo-3-R-pentanoic acid with a metal azide;

(e) converting the thus-produced ester of 5-azido-5-$R_1$-2-$R_2$-4-oxo-3-R-pentanoic acid with hydrogen and a lower alkanoic anhydride into an alkyl ester of 5-lower-alkanoylamino-5-$R_1$-2-$R_2$-4-oxo-3-R-pentanoic acid or, when the starting ester was the benzyl ester, into the corresponding free acid; and (f) subjecting the thus-produced 5-lower-alkanoylamino compound to acid hydrolysis to produce the corresponding 5-amino-3-oxo-pentanoic acid, R, $R_1$ and $R_2$ in each instance having the values given herein above and alkyl and lower alkanoic are of 1–4 carbon atoms.

In compound aspects, this invention relates to compounds of one of the following formulae:

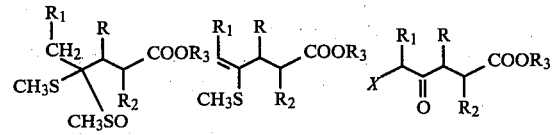

wherein R is $CF_3$, $CHF_2$ or $CH_2F$; $R_1$ is H or alkyl of 1 to 4 carbon atoms; $R_2$ is H, alkyl of 1 to 4 carbon atoms or benzyl; and $R_3$ is alkyl of 1 to 4 carbon atoms or benzyl and X is Br or $N_3$.

DETAILED DISCUSSION

The novel processes of this invention and the novel compounds produced therein can be illustrated by the following flow diagram.

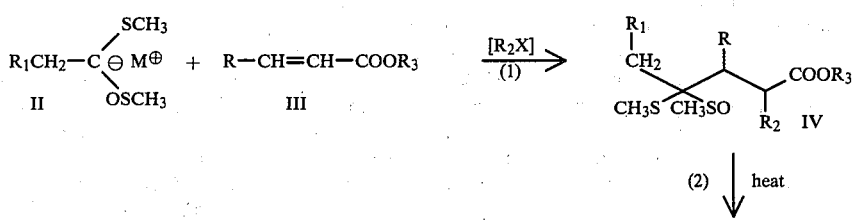

-continued

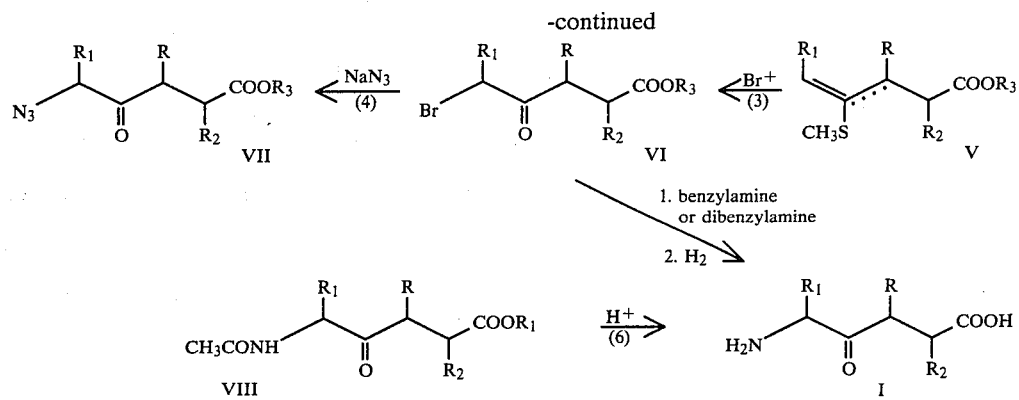

In the above formulae, R, $R_1$ and $R_2$ have the values given hereinabove, M is an alkali metal and $R_3$ is alkyl of 1–4 carbon atoms or benzyl. The individual reactions are described in more detail hereinbelow.

In the first step of the process of this invention, the starting methyl 1-(methylthio)-ethyl sulfoxides are known or can be produced according to procedures described in the literature. See, e.g., Ogura et al, Tetrahedron Letters, No. 34, 1971, pp. 3151–3154. Ethyl β-(trifluoromethyl)-acrylate is a known compound.

The benzyl and other lower alkyl esters of β-trifluoromethyl-,β-(difluoromethyl)- and β-(fluoromethyl)-acrylic acid can be prepared from the corresponding free acids [E. T. McBee et al, J. Org. Chem., 38, 632–6 (1973)] by treatment with the appropriate alcohol saturated with hydrogen chloride gas or from the acid and an O-benzyl or O-alkyl dialkylisourea.

The sulfoxide is reacted with an anhydrous metal base, e.g., an alkyllithium or alkylsodium, NaH, KH, lithium dialkylamide or triphenylmethylsodium, in an inert solvent, e.g., diethylether, tetrahydrofuran or glyme, at reduced temperature, e.g., −78° to 0° C. For the analogous reaction with methylthiomethyl sulfoxide, see Ogura et al, Tetrahedron Letters, No. 34, 1971, pp. 3151–3154.

The resulting metal derivative(II) is condensed with the selected γ-substituted-acrylic acid ester, also at such a reduced temperature. The reaction begins immediately and usually reaches completion in about 1–24 hours.

The thus-produced 4-(methylsulfinyl)-4-(methylthio)-substituted-pentanoic acid ester enolate anion can be treated with a proton source such as water or an alcohol to give the ester (IV, $R_2$=H) or the ester enolate anion can be treated in situ, e.g., with a $C_1$–$C_4$ alkyl iodide or bromide or with benzyl chloride, bromide or iodide to produce the corresponding ester wherein $R_2$ is alkyl of 1–4 carbon atoms or benzyl.

The thus-produced esters (IV) can be isolated, e.g., by decomposing any residual base and extracting the reaction mixture with ether or like solvent, washing, drying, and distilling off the solvent. The esters are usually obtained as oils which decompose upon distillation. Therefore, they preferably are converted without further purification to the corresponding unsaturated 4-(methylthio)-substituted ester (V). Moreover, preferably after decomposing any residual base remaining from the first step under anhydrous conditions, the reaction product (IV) can be converted without isolation or purification into the unsaturated ester (V) merely by heating the reaction mixture.

In the second step of the process of this invention, methylsulfinic acid is split out from the esters of step (1). This is conveniently accomplished by heating, e.g., at 60°–120° C., preferably under anhydrous conditions. The reaction usually reaches completion in about 4–10 hours, if conducted in the presence of a base which will react with the methylsulfinic acid as it is formed, e.g., $NaHCO_3$, $Na_2CO_3$ or $CaCO_3$.

This reaction produces the desired unsaturated ester (V) as a mixture with its $\Delta^3$-unsaturated isomer, which is preferably separated therefrom before the next step of the process, e.g., by column chromatography over silica gel or distillation. Alternatively, the isomeric mixture of esters can first be hydrolyzed to their corresponding free acids in a conventional manner, e.g., with aqueous base such as NaOH, $Na_2CO_3$ or $K_3PO_4$, with or without heating, e.g., to from 40°–100° C. The mixture of acids can be separated by distillation, chromatography and/or fractional crystallization.

If an ester group different from that of the starting γ-substituted acylic acid (III) is desired as the starting material for step (3) of the process of this invention, the thus-produced and purified free acid (V $R_3$=H) can be reesterified by means conventionally employed with unsaturated acids, e.g., by reaction of the free acid with the appropriate alcohol saturated with hydrogen chloride gas or by reaction of the free acid with an O-benzyl- or O-alkyldicyclohexylisourea.

In the next step of the process of this invention, the 4-methylthio substituted unsaturated ester (V) from step (2) is reacted with a source of positive bromine, e.g., an N-bromoamide or N-bromoimide, under aqueous conditions. 1,2-Addition of HOBr occurs across the double bond and methyl mercaptan splits off to yield the corresponding 5-bromo-4-oxo-ester (VI). It is known that vinyl sulfides can be converted to α-bromoketones with N-bromosuccinimide. See K. H. Geiss et al, Angew. Chim., 86, 484 (1974).

The thus-produced 5-bromo-4-oxo-pentanoic acid esters (VI) from step (3) can be converted by a variety of conventional methods into the corresponding 5-amino-4-oxo-pentanoic acids (VIII). In a preferred method, a benzyl ester (VI, $R_3$=$C_6H_5CH_2$) is converted to a corresponding azide (VII), e.g., with a metal azide such as sodium azide or potassium azide, and the azide catalytically hydrogenated in the presence of a lower-alkanoic acid anhydride, thereby simultaneously converting the azido group to an acylamido group and the benzyl ester group to a free acid group. The preferred anhydride is acetic anhydride, which forms an acetamido group. The hydrogenation is conducted under conditions mild enough to ensure the keto group is unaffected, e.g., at 0°–25° C. and 0–25 lbs/in² hydrogen pressure under the acidic conditions provided by the acid anhydride.

When a benzyl ester or the free acid of the azide derivative of a bromo compound of step (3) is thus hydrogenated, a 5-amino-4-oxo-pentanoic acid of Formula I is obtained. When an alkyl ester is thus hydrogenated, an alkyl ester of a 5-amino-4-oxo-pentanoic acid of Formula I is obtained, which can be hydrolyzed in a conventional manner, under mildly acidic conditions, to produce the corresponding free acid of Formula I.

Techniques conventional for the isolation of aminoacids can be employed to isolate and purify a thus-produced compound of Formula I, e.g., fractional crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

EXAMPLE 1

Ethyl 4-methylsulfinyl-4-methylthio-3-trifluoromethyl-pentanoate

To a stirring solution of 3.98 g (28.2 mole) of methyll-(thiomethyl)-ethyl sulfoxide in 35 ml in THF (30 ml) cooled to −78° C., add 14.2 ml of 2.2 M n-butyllithium in hexane (to produce 1-(methylsulfinyl)-1-(methylthio)-ethyllithium. After 1 hour at 0° C., cool the solution of the anion back to −78° C. and add 4.64 g (27.6 mmol) of ethyl β-trifluoromethylcrotonate in 15 ml of THF over a 5 minute period. After 15 minutes, treat with saturated aqueous NH$_4$Cl, dilute with ether, wash successively with water and brine, and dry over MgSO$_4$. After removal of the solvent under reduced (88%) of the desired product (IV, R=CF$_3$, R$_1$,R$_2$=H, R$_3$=C$_2$H$_5$) is obtained as an oil.

EXAMPLE 2

Ethyl 2-methyl-4-methylsulfinyl-4-methylthio-3-trifluoromethyl-pentanoate

Follow the procedure of Example 1 except, instead of quenching the reaction after 15 minutes, add methyl iodide (4.3 g, 30 mMole) and maintain the mixture overnight before quenching with aqueous NH$_4$Cl. The desired 2-methyl substituted Michael adduct (IV, R=CF$_3$, R$_1$=H, R$_2$=CH$_3$, R$_3$=C$_2$H$_5$) is obtained as an oil after washing, drying and removal of the solvent.

EXAMPLE 3

4-Methylthio-3-trifluoromethyl-4-pentenoic acid and ethyl and benzyl esters

Heat a solution of 15.3 g of the crude sulfoxide of Example 1 and 10.1 g of NaHCO$_3$ in 150 ml of glyme at reflux for 30 minutes to effect the elmination of methylsulfinic acid. Dilute the mixture with ether, wash successively with water and brine and dry over MgSO$_4$ to obtain, after removal of the solvent under reduced pressure, 13.3 g of a mixture of ethyl 4-methylthio-3-trifluoromethyl-4-pentenoate (V, R=CF$_3$, R$_1$,R$_2$,=H, R$_3$=C$_2$H$_5$) and ethyl 4-methylthio-3-trifluoromethyl-3-pentenoate.

Saponify the ester by the addition of 40 ml of methanol and 2 N NaOH followed by stirring first at 25° C. for 30 minutes and then at 60° C. for 5 minutes. Pour reaction mixture into a separatory funnel containing water and wash with ether. Acidify the aqueous layer with 18 ml of 6 N HCl and extract twice with ether. Wash the organic layer with brine, dry over MgSO$_4$, and remove the solvent under reduced pressure to obtain 9 g of oil. Bulb-to-bulb distillation of this oil at 150° C. and 0.1 torr yields 5 g of partially crystalline oil which is a mixture of the desired vinyl sulfide free acid (V, R=CF$_3$, R$_1$, R$_2$, R$_3$=H) and 4-methylthio-3-trifluoromethyl-3-pentenoic acid.

To a solution of 3.37 g (15.5 mmol) of the distilled vinyl sulfide free acid in 4 ml of CH$_2$Cl$_2$ add 5.15 g (16.4 mmol) of O-benzyl-dicyclohexyl isourea in 5 ml CH$_2$Cl$_2$. After stirring for 72 hours, filter the mixture, dilute with ether, wash successively with 0.2 N HCl, saturated aqueous NaHCO$_3$, and brine, and dry over MgSO$_4$. Evaporate the solvent in vacuo to obtain 5.7 g of benzyl 4-methylthio-3-trifluoromethyl-4-pentenoate as an oil which also contains some isourea.

EXAMPLE 4

2-Methyl-4-methylthio-3-trifluoromethyl-4-pentenoic acid and ethyl and benzyl esters.

Follow the procedure of Example 3 with the crude sulfoxide of Example 2 to obtain 2-methyl-4-methylthio-3-trifluoromethyl-4-pentenoic acid (V, R=CF$_3$, R$_1$,R$_3$=H, R$_2$=CH$_3$) and its ethyl and benzyl esters.

EXAMPLE 5

Benzyl-5-bromo-4-oxo-3-trifluoromethyl-pentanoate

To a stirring solution of 2.88 g (16 mmol) of NBS in 40 ml of 20% aqueous CH$_3$CN cooled to 0° C. add dropwise 1.06 g of the benzyl ester of Example 3 in 4 ml of CH$_3$CN. After 15 minutes of stirring pour the reaction mixture into a separatory funnel containing aqueous NaHSO$_3$ and extract with ether. Wash the organic layer with brine and dry over MgSO$_4$ to give, after the evaporation of the solvent and flash chromatography (10% EtOAc:Hexanes), 290 mg of the desired benzyl ester (IV, R=CF$_3$, R$_1$,R$_2$=H, R$_3$=C$_6$H$_5$CH$_2$).

EXAMPLE 6

Benzyl 2-methyl-5-bromo-4-oxo-3-trifluoromethyl-pentanoate

Follow the procedure of Example 5 with the benzyl ester of Example 4 to obtain the desired 2-methyl substituted benzyl ester (VI, R=CF$_3$, R$_1$,=H, R$_2$=CH$_3$, R$_3$=C$_6$H$_5$CH$_2$).

EXAMPLE 7

Benzyl 5-azido-4-oxo-3-trifluoromethyl-pentanoate

Stir a mixture of 290 mg (0.82 mmol) of the bromo-ketoester of Example 5, 91 mg (1.4 mmol) of NaN$_3$, and 4 ml of dry DMF at 25° C. for 1 hour. Dilute the mixture with ether, wash several times with water and then brine, dry over MgSO$_4$, and remove the solvent in vacuo to give 210 mg of the desired azide (VII, R=CF$_3$, R$_1$,R$_2$=H, R$_3$=C$_6$H$_5$CH$_2$) as an oil.

EXAMPLE 8

Benzyl 2-methyl-5-azido-4-oxo-3-trifluoromethyl-pentanoate

Follow the procedure of Example 7 with the bromo-ketoester of Example 6 to obtain the 2-methyl-substituted azide (VII, $R=CF_3$, $R_1=H$, $R_2=CH_3$, $R_3=C_6H_5CH_2$).

EXAMPLE 9

5-Acetamido-4-oxo-3-trifluoromethyl-pentanoic acid

To a stirring solution of 195 mg of the azide of Example 7 in 5 ml of ethyl acetate add 70 mg of 10% Pd/C. After 15 minutes of stirring at 25° C., filter the solution through celite and evaporate under reduced pressure to afford purified azide. Hydrogenate a stirred solution of the purified azide in 6 ml of ethyl acetate and 2 ml of $Ac_2O$ containing 190 mg of 10% Pd/C at atmospheric pressure and 26° C. until no azide remains (determined by IR of aliquot). After filtration thru celite and removal of the solvent, chromatograph the residue on silica gel (88:10:2-$CHCl_3$:MeOH:HOAc) to afford 27 mg of the desired 5-acetamido-substituted acid (VIII, $R=CF_3$, $R_1$, $R_2=H$) as a brown oil.

EXAMPLE 10

2-Methyl-5-acetamido-4-oxo-3-trifluoromethyl-pentanoic acid

Follow the procedure of Example 9 with the 2-methyl-substituted azide of Example 8 to obtain the desired 2-methyl-substituted acid (VIII, $R=CF_3$, $R_1=H$, $R_2=CH_3$).

EXAMPLE 11

5-Amino-4-oxo-3-trifluoromethyl-pentanoic acid

Heat a mixture of 100 mg of the acetamide obtained in Example 9 in 15 ml of methanol and 15 ml of 6 N hydrochloric acid under reflux for 4 hours and then remove the solvent under reduced pressure. Recrystallize the residue from ethanol-ether to give the desired 5-amino compound (I, $R=CF_3$, $R_1=H$, $R_2=H$) as the hydrochloride salt.

EXAMPLE 12

2-Methyl-5-amino-4-oxo-3-trifluoromethyl-pentanoic acid

Follow the procedure of Example 10 with the 2-methyl substituted acid of Example 10 to obtain the desired 2-methyl-5-amino-acid (I, $R=CF_3$, $R_1=H$, $R_2=CH_3$).

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of the formula

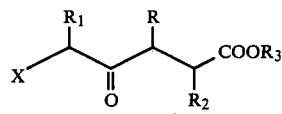

wherein R is $CF_3$, $CHF_2$ or $CH_2F$; $R_1$ is H or alkyl of 1 to 4 carbon atoms; $R_2$ is H, alkyl of 1 to 4 carbon atoms or benzyl; $R_3$ is alkyl of 1 to 4 carbon atoms or benzyl and X is $N_3$.

2. A compound according to claim 1 wherein R is $CF_3$.

3. A compound according to claim 1 wherein $R_1$ is H.

4. A compound according to claim 1 wherein $R_2$ is H.

5. Benzyl 5-azido-4-oxo-3-trifluoromethyl-pentanoate, a compound of claim 1.

* * * * *